(12) United States Patent
Anderskewitz

(10) Patent No.: US 6,291,531 B1
(45) Date of Patent: Sep. 18, 2001

(54) LTB$_4$ ANTAGONIST, PROCESSES FOR THE PREPARATION THEREOF AND ITS USE AS A PHARMACEUTICAL COMPOSITION

(75) Inventor: Ralf Anderskewitz, Bingen (DE)

(73) Assignee: Boehringer Ingelheim Pharma KG, Ingelheim, DE (US)

( * ) Notice: Subject to any disclaimer, the term of this patent is extended or adjusted under 35 U.S.C. 154(b) by 0 days.

(21) Appl. No.: 09/663,297

(22) Filed: Sep. 15, 2000

Related U.S. Application Data

(63) Continuation of application No. 60/161,264, filed on Oct. 25, 1999.

(30) Foreign Application Priority Data

Oct. 7, 1999 (DE) .............................. 199 48 428

(51) Int. Cl.$^7$ ................................. A61K 31/155
(52) U.S. Cl. .......................................... 514/637; 564/244
(58) Field of Search .............................. 564/244; 514/637

(56) References Cited

U.S. PATENT DOCUMENTS 5,731,332 * 3/1998 Anderskewitz et al. ............. 514/354
6,197,824 * 3/2001 Schromm et al. ................... 514/637

* cited by examiner

*Primary Examiner*—Samuel Barts
(74) *Attorney, Agent, or Firm*—R. P. Raymond; M-E. M. Devlin

(57) ABSTRACT

The present invention relates to a new LTB$_4$ antagonist, processes for the preparation thereof and its use as a pharmaceutical composition.

4 Claims, No Drawings

LTB₄ ANTAGONIST, PROCESSES FOR THE PREPARATION THEREOF AND ITS USE AS A PHARMACEUTICAL COMPOSITION

This application is a continuation of No. 60/167,264 filed Oct. 25, 1999.

The present invention relates to a new $LTB_4$ antagonist, processes for preparing it and its use as a pharmaceutical composition.

$LTB_4$ antagonists are known from the prior art. Thus, International Patent Application WO 98/11062 discloses benzamidine derivatives having the abovementioned pharmacological activity.

Surprisingly, it has been found that the new $LTB_4$ antagonist according to the invention has superior properties to the compounds known from the prior art. In this context the exceptionally high in vitro and in vivo activity as well as the surprisingly high metabolic stability of the new $LTB_4$ antagonist according to the invention should be mentioned.

The $LTB_4$ antagonist according to the invention is the compound of formula (I)

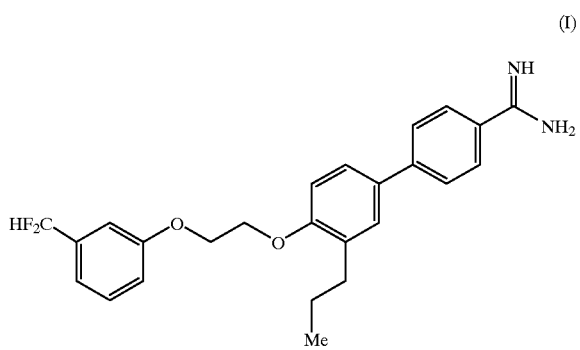

optionally in the form of the pharmacologically acceptable acid addition salts thereof. As mentioned above, the compound of formula (I) can be converted into the salts thereof, particularly for pharmaceutical use into the physiologically and pharmacologically acceptable salts thereof with an inorganic or organic acid. Suitable acids for this purpose include hydrochloric acid, hydrobromic acid, sulphuric acid, phosphoric acid, methanesulphonic acid, acetic acid, fumaric acid, succinic acid, lactic acid, citric acid, tartaric acid or maleic acid. In addition, mixtures of the abovementioned acids can be used.

As has been found, the compound of formula I is characterised by its versatility of use in the therapeutic field. Particular emphasis should be laid on those applications for which the $LTB_4$-receptor-antagonistic properties play a part.

The following should be mentioned in particular: arthritis, asthma, chronic obstructive lung diseases such as chronic bronchitis, psoriasis, ulcerative colitis, gastro- or enteropathy induced by nonsteroidal antiphlogistics, cystic fibrosis, Alzheimer's disease, shock, reperfusion damage/ischaemia, atherosclerosis, multiple sclerosis.

The new compounds may also be used to treat illnesses or conditions in which the passage of cells from the blood through the vascular endothelium into the tissues is of importance (such as metastasis) or illness and conditions in which the combination of $LTB_4$ or another molecule (such as 12-HETE) with the $LTB_4$ receptor has an influence on cell proliferation (e.g. chronic myeloid leukaemia).

The new compound may also be used in conjunction with other active substances, e.g. those which are used for the same indications, or e.g. with antiallergic agents, secretolytics, $\beta_2$-adrenergics, steroids taken by inhalation, antihistamines and/or PAF antagonists. They may be administered topically, orally, transdermally, nasally, parenterally or by inhalation.

The activity can be investigated pharmacologically and biochemically using tests as disclosed for example in WO 93/16036, pp. 15 to 17; reference is hereby made to the contents of this publication.

The therapeutic or prophylactic dose depends—apart from the potency of the individual compounds and the patient's body weight—on the nature and gravity of the condition. For oral administration the dosage is between 10 and 500 mg, preferably between 20 and 250 mg. By inhalation the amount of active substance delivered to the patient is between about 0.5 and 25, preferably between about 2 and 20 mg.

Solutions for inhalation generally contain between about 0.5 and 5% of active substance. The new compounds may be administered in conventional preparations, e.g. as plain or coated tablets, capsules, lozenges, powders, granules, solutions, emulsions, syrups, aerosols for inhalation, ointments and suppositories.

The following Examples show some possible ways of formulating the preparations:

| Tablets | |
|---|---|
| Composition: | |
| Active substance according to the invention | 20 parts by weight |
| Stearic acid | 6 parts by weight |
| Glucose | 474 parts by weight |

The ingredients are processed in the usual way to form tablets weighing 500 mg. If desired, the active substance content may be increased or reduced and the quantity of glucose reduced or increased accordingly.

| Suppositories | |
|---|---|
| Composition: | |
| Active substance according to the invention | 100 parts by weight |
| Powdered lactose | 45 parts by weight |
| Cocoa butter | 1555 parts by weight |

The ingredients are processed in the usual way to form suppositories weighing 1.7 g.

3. Powder for Inhalation

Micronised powdered active substance (compound of formula I; particle size about 0.5 to 7 μm) are packed into hard gelatine capsules in quantities of 5 mg, optionally with the addition of micronised lactose. The powder is inhaled from conventional inhalers, e.g. according to DE-A 33 45 722, to which reference is hereby made.

The new compound may be obtained analogously to methods of synthesis known from the prior art for preparing structurally comparable benzamidine derivatives. At this point reference is made particularly to the method of preparation disclosed by International Patent Application WO 98/11062, which describe, inter alia, the method of synthesising benzamidine derivatives by reducing the corresponding amidoximes, by aminolysis of the corresponding imino ester and by reacting suitably substituted phenols with aryloxyalkyls substituted by a nucleofugic leaving group in the manner of a Williamson ether synthesis.

Alternatively, the compound of formula (I) according to the invention may be obtained, for example, by reacting the nitrile of formula (II)

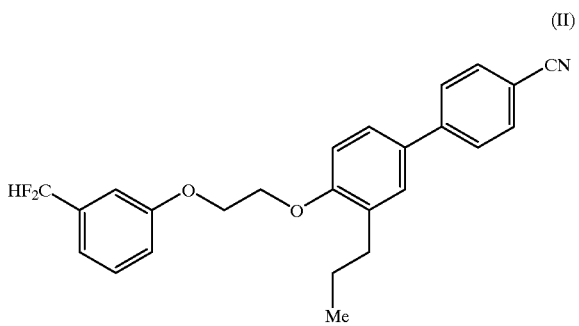

with Li-hexamethyldisilazane. For the reaction it is appropriate to use non-polar and polar aprotic solvents such as toluene, ether, tetrahydrofuran at temperatures from −80° C. to 120° C. To cleave the silyl groups, inorganic and organic acids are used such as HCl, HBr, $H_2SO_4$, sulphonic acids such as p-toluenesulphonic acid, benzenesulphonic acid or methanesulphonic acid and carboxylic acids such as formic acid, acetic acid or trifluoroacetic acid at temperatures from 0° C. to 100° C.

The compound according to the invention may be prepared, starting from compounds known from the prior art, inter alia using the process described in the following synthesis example. Various other embodiments of the process will be apparent to anyone skilled in the art from the present specification and from the abovementioned International Patent Application WO 98/11062; reference is hereby made to the contents of this publcation. It is specifically pointed out that the following synthesis example is provided solely as an illustration and not as a restriction to the invention.

SYNTHESIS EXAMPLE

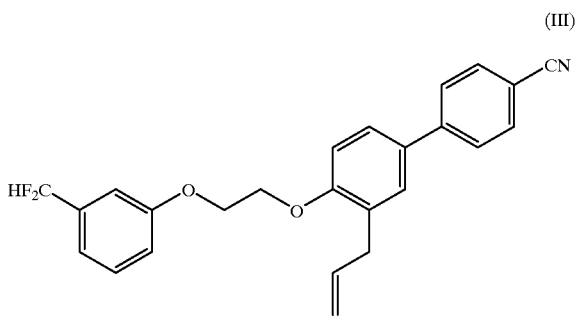

1 g of the nitrile (III) were placed in 20 ml of ethanol and a solution of 700 mg of hydroxylamine hydrochloride, 590 mg of $Na_2CO_3$ in 3 ml of $H_2O$ was slowly added dropwise while refluxing. The mixture was then boiled for 4 h and after cooling the crystals precipitated were suction filtered and washed with $H_2O$. After neutralisation with 260 mg of methanesulphonic acid in 5 ml of ethanol, precipitation was carried out with diethylether and the precipitate was suction filtered. The substance was hydrogenated in 50 ml of methanol with the addition of 200 mg of Pd/C (5%) at normal pressure. After the catalyst had been suction filtered, Raney Ni was added and hydrogenation was carried out again. The catalyst was suction filtered, the solvent was distilled off, the residue was dissolved in a little ethanol and precipitated with diethylether. Yield: 830 mg. Mp.: 204–205° C. (as the methanesulphonate).

What is claimed is:

1. A compound of formula (I)

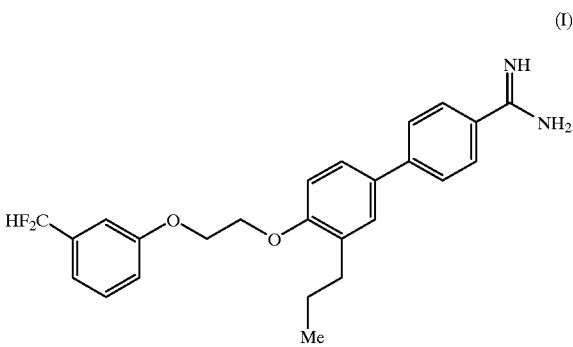

, or a pharmacologically acceptable acid addition salt thereof.

2. A pharmaceutical composition of matter comprising a compound of formula (I) according to claim 1 together with a pharmaceutically acceptable excipient or carrier.

3. A method of treating disease in a warm-blooded animal, which disease involves $LTB_4$ activity, which comprises administering to the animal a therapeutically effective amount of a compound according to claim 1.

4. The method as recited in claim 3 wherein the disease is selected from the group consisting of arthritis, asthma, chronic obstructive lung diseases psoriasis, ulcerative colitis, gastro- or enteropathy induced by nonsteroidal antiphlogistics, cystic fibrosis, Alzheimer's disease, shock, reperfusion damage and ischaemia, atherosclerosis, and multiple sclerosis.

* * * * *